United States Patent [19]
Ikeda et al.

[11] Patent Number: 6,034,232
[45] Date of Patent: Mar. 7, 2000

[54] STRESS PROTEINS

[75] Inventors: Jun Ikeda, Tokyo; Sumiko Kaneda, Kyoto; Hideki Yanagi, Takarazuka; Masayasu Matsumoto, Mino; Takashi Yura, Kyoto, all of Japan

[73] Assignee: HSP Research Institute, Inc., Osaka, Japan

[21] Appl. No.: 09/175,581

[22] Filed: Oct. 20, 1998

Related U.S. Application Data

[62] Division of application No. 08/770,301, Dec. 20, 1996, Pat. No. 5,948,637.

[30] Foreign Application Priority Data

Dec. 20, 1995 [JP] Japan .................................. 7-349661
Jul. 23, 1996 [JP] Japan .................................. 8-213181

[51] Int. Cl.⁷ .......................... C12N 15/67; C12N 15/12; C12N 15/85
[52] U.S. Cl. .................. 536/24.1; 536/23.5; 435/69.1; 435/252.3
[58] Field of Search .............................................. 536/24.1

[56] References Cited

U.S. PATENT DOCUMENTS

| | | | |
|---|---|---|---|
| 5,139,954 | 8/1992 | Litts et al. | 435/320.1 |
| 5,612,318 | 3/1997 | Weichselbaum et al. | 514/44 |
| 5,659,024 | 8/1997 | Reed et al. | 536/24.1 |
| 5,681,706 | 10/1997 | Anderson et al. | 435/6 |
| 5,770,717 | 6/1998 | Golemis et al. | 536/23.2 |
| 5,814,517 | 9/1998 | Seidel et al. | 435/325 |

FOREIGN PATENT DOCUMENTS

0683230A1 11/1995 European Pat. Off. .

OTHER PUBLICATIONS

Chen et al., Database EMROD, EMBL, Entry CG34206, Genbank Acc. No. U34206, 28, Sep., 1995, *Cricetulus griseus* 170 kDa glucose regulated protein (grp170) mRNA, complete cds, XP002060254.

Chen et al., The 170 kDa glucose regulated stress protein is a large HSP70–, HSP110–like protein of the endoplasMic reticulum, FEBS Letters, 380 1996) pp. 68–72.
Hori et al, Journal of Neurochemistry, vol. 66, No. 3, pp. 973–979 (1996).
Ogawa et al, J. Clin. Invest., vol. 85, pp. 1090–1098 (1990).
Tam, Proc. Natl. Acad. Sci. USA, vol. 85, pp. 5409–5413 (1988).
Maeda et al, J. Exp. Med., vol. 180, pp. 2297–2308 (1994).
Chomczynski et al, Analytical Biochemistry, vol. 162, pp. 156–159 (1987).
Pelham, Trends Biochem. Sci., vol. 15, pp. 483–486 (1990).
Kuwabara et al, The Journal of Biological Chemistry, vol. 271, No. 9, pp. 5025–5032 (1996).
Altschul et al, J. Mol. Biol., vol. 215, pp. 403–410 (1990).
Pearson et al., Proc. Natl. Acad. Sci. USA, vol. 85, pp. 2444–2448 (1988).
Hunt et al, Proc. Natl. Acad. Sci. USA, vol. 82, pp. 6455–6459 (1985).
DeLuca–Flaherty et al, Nucleic Acids Research, vol. 18, No. 18, p. 5569 (1990).
Lee–Yoon et al, The Journal of Biological Chemistry, vol. 270, No. 26, pp. 15725–15733 (1995).

(List continued on next page.)

*Primary Examiner*—Ponnathapu Achutamurthy
*Assistant Examiner*—William W. Moore
*Attorney, Agent, or Firm*—Birch, Stewart, Kolasch & Birch, LLP

[57] ABSTRACT

A polypeptide obtainable by inducement under hypoxic conditions having a sequence comprising:
(a) the amino acid sequence of SEQ ID NO:1 or 3 or a fragment thereof; (b) an amino acid sequence encoded by the nucleotide sequence of SEQ ID NO: 2 or 4 or a fragment thereof; or (c) an amino acid sequence resulting from deletion, addition, insertion or substitution of one or more amino acids in the amino acid sequence of SEQ ID NO:1 or 3; a polynucleotide encoding the above polypeptide or the fragment thereof useful for producing the above polypeptide by a biotechnological technique; and an antibody or fragment thereof specifically binding the above polypeptide.

2 Claims, 3 Drawing Sheets

OTHER PUBLICATIONS

Bairoch et al, Nucleic Acids Research, vol. 22, No. 17, pp. 3853–3859 (1994).

Bork et al, Proc. Natl. Acad. Sci. USA, vol. 89, pp. 7290–7294 (1992).

Naved et al., CBP–140, a Novel Endoplasmic Reticulum Resident, etc., Cell Structure and Function, 20: 133–141 (1995) by Japan Society for Cell Biology.

Kuwabara et al., Database EMROD, EMBL, Entry RNU41853, Genbank Acc. No. U41853, (1996) *Rattus Norvegicus* 150 kDa oxygen regulated protein (ORP150) mRNA, complete cds., XP002060255.

Tsukamoto et al., 150–kD Oxygen–regulated Protein Is Expressed in Human Atherosclerotic Plaques, etc., Journal Of Clinical Investigations, vol. 98, No. 8, (1996) pp. 1930–1941.

Rippmann et al, The EMBO Journal, vol. 10, No. 5, pp. 1053–1059 (1991).

Lin et al, Molecular Biology of the Cell, vol. 4, pp. 1109–1119 (1993).

Chen et al, FEBS Letters, vol. 380, pp. 68–72 (1996).

Heacock et al., Enhanced synthesis of stress proteins caused by hypoxia and relation to altered cell growth and metabolism, British Journal of Cancer, vol. 62, No. 2 (1990) pp. 217–225.

Lieuallen et al., Database EMEST10, EMBL, Entry HSW18185, Genbank Acc. No. W18185, (1966) Image:20073 Soares infant brain 1NIB *Homo sapiens* cDNA clone 20073, XP002060256.

English translation of Matsumoto et al., Experimental Medicine, vol. 13, "Brain ischemia and stress proteins", pp. 63–68, 1995.

Ono, M., et al., Nucleic Acids Research, vol. 15, "A novel human nonviral retroposon derived from an endogenous retrovirous", pp. 8725–8737, 1987.

Butler, A.J., et al., The Journal of Biological Chemistry, vol. 266, "Induction of the proliferative phenotype in differentiated myogenic cells by hypoxia," pp. 18250–18258, 1991.

Roll, D.E., et al., Molecular and Cellular Biochemistry, vol. 103, "oxygen regulated 80kDa protein and glucose regulated 78 kDA protein are identical", pp. 141–148, 1991.

Matsumoto, M., et al., Experimental Medicine (Japan), vol. 13, "Brain ischemia and stress proteins", pp. 63–68, 1995.

Smith, H.C., et al., in Cell Biology of Trauma LeMasters, J.J., et al., Eds., CRC Press, Inc. "Alteration in cell cycle control factors and the induction of oxygen–regulated proteins by hypoxic stress", pp. 213–225, 1995.

Ayoubi, T.A.K., et al., The Journal of Biological Chemistry, vol. 269, "Expression of the dibasic proprotein processing enzyme furin is directed by multiple promoters", pp. 9298–9303, 1994.

Hagan, D.L., et al., The Journal of Biological Chemistry, vol. 269, "Transcriptional regulation of human and hamster microsomal triglyceride transfer protein genes", pp. 28737–28744, 1994.

Jerkins, A.A., et al., The Journal of Biological Chemistry, vol. 270, "Characterization of the murine mitochondrial glycerol–3–phosphate acytransferase promoter", pp. 1416–1421, 1995.

Bai, G., et al., The Journal of Biological Chemistry, vol. 270, "Functional analysis of the proximal 5'–flanking region of the N–methyl–D–aspartate receptor subunit gene, NMDAR1", pp. 7737–7744, 1995.

Myers, R.L., et al., The Journal of Biological Chemistry, vol. 270, "Functional characterization of the brain–specific FGF–1 promoter, FGF–1B*", pp. 8257–8266, 1995.

Figueiredo, M.S., et al., The Jourhal of Biological Chemistry, vol. 270, "cis–acting elements and transcription factors involved in the promoter activity of the human factor VIII gene", pp. 11828–11838, 1995.

Pang, J.–W.S., et al., The Journal of Biological Chemistry, vol. 270, "Functional characterization of the promoter region of the platelet–activating factor receptor gene", pp. 14123–14129, 1995.

Strannick, K.S., et al., The Journal of Biological Chemistry, vol. 270, "Transcription of the murine interlekin 5 gene is regulated by multiple promoter elements", pp. 20575–20582, 1995.

Patterson, C., et al., The Journal of Biological Chemistry, vol. 270, "Cloning and functional analysis of the promoter for KDR/flk–1, a receptor for vascular endothelial growth factor", pp. 23111–23118, 1995.

STRESS PROTEINS

This application is a divisional of application Ser. No. 08/770,301, filed on Dec. 20, 1996, and issued as U.S. Pat. No. 5,948,637, the entire contents of which are hereby incorporated by reference.

BACKGROUND OF THE INVENTION

1. Field of the Invention

The present invention relates to an oxygen-regulated protein 150 (ORP150). Specifically, the invention relates to the amino acid sequence of human ORP150, polynucleotides encoding human ORP150, promoters of human ORP150 gene and antibodies specific to human ORP150.

2. Discussion of the Related Art

Since the expression of a 70 kDa heat shock protein (HPS70) in cerebral ischemic lesions was reported for the first time, various stress proteins, represented by HSP70, have been reported to be expressed in myocardial ischemic and atherosclerotic lesions, as well as cerebral ischemic lesions. The fact that the induction of HSP, a mechanism of defence against heat stress, is seen in ischemic lesions, suggests that the stress response of the body to ischemic hypoxia is an active phenomenon involving protein neogenesis. Regarding cultured cells, stressful situations that cause ischemia in vivo, such as hypoglycemia and hypoxia, have been shown to induce a group of non-HSP stress proteins, such as glucose-regulated protein (GRP) and oxygen-regulated protein (ORP).

ORP is therefore expected to serve in the diagnosis and treatment of ischemic diseases.

Hori et al. have recently found that exposure of cultured rat astrocytes to hypoxic conditions induces 150, 94, 78, 33 and 28 kDa proteins [J. Neurochem., 66, 973–979(1996)]. These proteins, other than the 150 kDa protein, were identified as GRP94, GRP78, hemoxygenase 1 and HSP28, respectively, while the 150 kDa protein (rat ORP150) remains not to be identified. In addition, there has been no report of human ORP150 protein.

SUMMARY OF THE INVENTION

Accordingly, the object of the present invention is to provide human and rat ORP150 proteins and the amino acid sequence-thereof as well as nucleotide sequences encoding the proteins.

Another object of the present invention is to provide a nucleotide sequence which functions as a promoter for the human ORP150 gene.

It is still another object of the present invention is to provide antibodies against human ORP150 protein or fragments thereof which are useful in the diagnosis and treatment for ischemic diseases.

In one embodiment, the present invention relates to a polypeptide obtainable by inducement under hypoxic conditions having a sequence comprising:
(a) the amino acid sequence of SEQ ID NO:1 or 3 or a fragment thereof;
(b) an amino acid sequence encoded by the nucleotide sequence of SEQ ID NO:2 or 4 or a fragment thereof; or
(c) an amino acid sequence resulting from deletion, addition, insertion or substitution of one or more amino acids in the amino acid sequence of SEQ ID NO:1 or 3.

In another embodiment, the present invention relates to a polynucleotide encoding the polypeptide of the above embodiment.

In still another embodiment, the present invention relates to a polynucleotide capable of hybridizing to the above polynucleotide or a fragment thereof and having promoter activity.

In still another embodiment, the present invention relates to a recombinant DNA which contains a nucleotide sequence of the present invention.

In still another embodiment, the present invention relates to an expression vector which contains the recombinant DNA of the present invention.

In still another embodiment, the present invention relates to an antibody or fragment thereof which specifically binds to the polypeptide of the present invention.

DETAILED DESCRIPTION OF THE INVENTION

Figure 1:
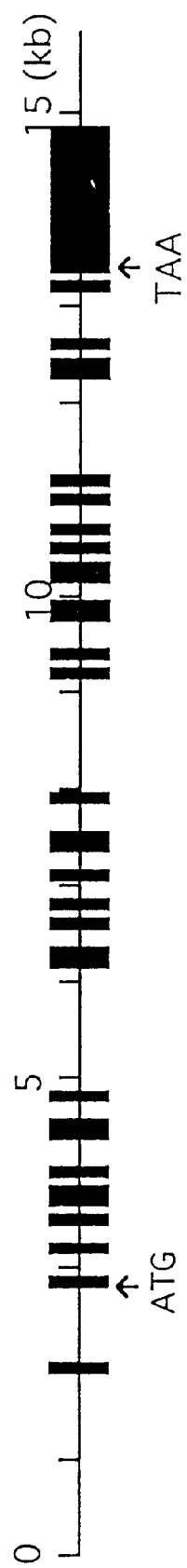
FIG. 1 indicates a schematic diagram of the exon-intron structure of the human ORP gene. Black squares represent the exons.

One embodiment of a polypeptide of the present invention is a polypeptide comprising the amino acid sequence shown by SEQ ID NO:1 in the sequence listing, and constituting the human oxygen-regulated-protein ORP150 which is obtainable by inducement under hypoxic conditions. Another embodiment of a polypeptide of the present invention is a polypeptide comprising the amino acid sequence shown by SEQ ID NO:3 in the sequence listing, and constituting the rat oxygen-regulated protein ORP150 which is obtainable by inducement under hypoxic conditions. The polypeptides of the present invention also include polypeptides each comprising a portion of the above-described polypeptides, and those containing the entire or portion of the above-described polypeptides. It is a well-known fact that mutation occurs in nature; some of the amino acids of ORP150 protein may be replaced or deleted, and other amino acids may be added or inserted. Mutation can also be induced by gene engineering technology. It is therefore to be understood that substantially homologous polypeptides resulting from such mutations in one or more amino acid residues are also included in the scope of the present invention as long as they are obtainable by inducement under hypoxic conditions.

One embodiment of a polynucleotide of the present invention is a polynucleotide encoding any one of the above-described polypeptides. Specifically, said polynucleotide is exemplified by the polynucleotide comprising the nucleotide sequence shown by SEQ ID NO:2 in the sequence listing, i.e., human ORP150 cDNA. The polynucleotide comprising the nucleotide sequence shown by SEQ ID NO:4 in the sequence listing is also included in the scope of the present invention. This polynucleotide is rat ORP150 cDNA. Polynucleotides comprising a portion of these polynucleotides, and those containing the entire or portion of these polynucleotides are also included in the scope of the present invention. As stated above, the ORP150 gene may have some bases replaced, deleted, added or inserted by mutations, and the resulting polynucleotides with partially different nucleotide sequences are also included in the scope of the present invention, as long as they are substantially homologous and encode a polypeptide obtainable by inducement under hypoxic conditions.

Another embodiment of a polynucleotide of the present invention is a polynucleotide comprising or containing the entire or portion of the nucleotide sequence shown by SEQ ID NO:12 in the sequence listing. This is a polynucleotide containing the promoter region of the human ORP150 gene. Polynucleotides capable of hybridizing to this polynucleotide under conventional hybridizing conditions (e.g., in 0.1×SSC containing 0.1% SDS at 65° C.) and possessing promoter activity are also included in the scope of the present invention. Successful cloning of said promoter region would dramatically advance the functional analysis of the human ORP150 gene and facilitate its application to the treatment of ischemic diseases.

The term "promoter" as used herein is defined as a polynucleotide comprising a nucleotide sequence that activates or suppresses the transcription of a desired gene by being present upstream or downstream of said gene.

The term "recombinant DNA" as used herein is defined as any DNA containing a polynucleotide described above.

The term "expression vector" as used herein is defined as any vector containing the recombinant DNA of the present invention and expressing a desired protein by introduction into the appropriate host.

The term "clone" as used herein means not only a cell into which a polynucleotide of interest has been introduced but also the polynucleotide of interest itself.

The term "inducement under hypoxic conditions" used herein means an increase in protein synthesis upon exposing cells to an oxygen-depleted atmosphere.

The amino acid sequences and nucleotide sequences of the present invention can, for example, be determined as follows: First, poly(A)⁺ RNA is prepared from rat astrocytes exposed to hypoxic conditions. After cDNA is synthesized from said poly(A)⁺RNA using-random hexamer primers, a cDNA library is prepared using the pSPORT1 vector (produced by Life Technology), or the like.

Next, PCR is conducted using oligonucleotide primers synthesized on the basis of the nucleotide sequence of the pSPORT1 vector used to prepare the cDNA library above and the degenerate nucleotide sequences deduced from the N-terminal amino acid sequence of purified rat ORP150, to yield a large number of amplified DNA fragments. These DNA fragments are then inserted into the pT7 Blue vector (produced by Novagen), or the like, for cloning to obtain a clone having nucleotide sequence which perfectly encodes the N-terminal amino acid sequence. Purification of ORP150 can be achieved by commonly used methods of protein purification, such as column chromatography and electrophoresis, in combination as appropriate.

In addition, by screening the above-described rat astrocyte cDNA library by colony hybridization using the insert in above clone as a probe, a clone having an insert thought to encode rat ORP150 can be obtained. This clone is subjected to stepwise deletion from both the 5'- and 3'-ends, and oligonucleotide primers prepared from determined nucleotide sequences are used to determine the nucleotide sequence sequentially. If the clone thus obtained does not encode the full length of rat ORP150, an oligonucleotide probe is synthesized on-the basis of the nucleotide sequence of the 5'- or 3'-region of the insert, followed by screening for a clone containing the nucleotide sequence extended further in the 5' or 3' direction, for example, the Gene Trapper cDNA Positive Selection System Kit (produced by Life Technology) based on hybridization using magnetic beads. The full-length cDNA of the rat ORP150 gene is thus obtained.

Separately, the following procedure is followed to obtain a human homologue of rat ORP150 cDNA. Poly(A)⁺RNA is prepared from the human astrocytoma U373 exposed to hypoxic conditions. After cDNA is synthesized from said poly(A)⁺RNA using random hexamer primers and an oligo (dT) primer, said cDNA is inserted into the EcoRI site of the pSPORT1 vector to prepare a cDNA library. Human ORP150 cDNA is then obtained using the Gene Trapper Kit and the nucleotide sequence is determined in the same manner as with rat ORP150 above.

The nucleotide sequence of human ORP150 cDNA is thus determined as that shown by SEQ ID NO:2 in the sequence listing, based on which the amino acid sequence of human ORP150 is determined.

Exposure of astrocytes to hypoxic conditions can, for example, be achieved by the method of Ogawa et al. [Ogawa, S., Gerlach, H., Esposito, C., Mucaulay, A. P., Brett, J., and Stern, D., J. Clin. Invest., 85, 1090–1098 (1990)].

Furthermore, the following procedure is followed to obtain human ORP150 genomic DNA. A genomic library purchased from Clontech (derived from human placenta, Cat. #HL1067J) is used. Screening is conducted by hybridization using a DNA fragment consisting of 202 bp of the 5' untranslated region and 369 bp of the coding region, derived from the rat cDNA clone, as well as a 1351 bp DNA fragment containing the termination codon, derived from the human cDNA, as probes. Two clones containing the ORP150 gene are isolated, one containing exons 1 through 24 and the other containing exons 16 through 26; the entire ORP150 gene is composed by combining these two clones. The nucleotide sequence of the 15851 bp human ORP150 genomic DNA is determined; its nucleotide sequence from the 5'-end to just before the translation initiation codon ATG in exon 2 is shown by SEQ ID NO:12 in the sequence listing.

As stated above, the present invention includes polypeptides containing the entire or portion of the polypeptide (human ORP150) having the amino acid sequence shown by SEQ ID NO:1 in the sequence listing. The present invention also includes the entire or portion of the polypeptide having the amino acid sequence shown by SEQ ID NO:1 in the sequence listing; for example, polynucleotides containing the entire or portion of the nucleotide sequence shown by SEQ ID NO:2 in the sequence listing are included in the scope of the present invention. The present invention also includes specific antibodies against these polypeptides of the present invention, and fragments thereof. The polypeptides of the present invention, polynucleotides encoding them, and specific antibodies against these polypeptides or fragments thereof are useful in the diagnosis and treatment of ischemic diseases, permitting utilization for the development of therapeutic drugs for ischemic diseases.

An antibody against a polypeptide of the present invention, which polypeptide contains the entire or portion of human or rat ORP150, can be prepared by a conventional method [Current Protocols in Immunology, Coligan, J. E. et al. eds., 2.4.1–2.4.7, John Wiley & Sons, New York (1991)]. Specifically, a rat ORP150 band, separated by, for example, SDS-polyacrylamide gel electrophoresis, is cut out and given to a rabbit etc. for immunization, after which blood is collected from the immunized animal to obtain an antiserum. An IgG fraction can be obtained if necessary by affinity chromatography using immobilized protein A, or the like. A peptide identical to the partial amino acid sequence of ORP150 can be chemically synthesized as a multiple antigen peptide (MAP) [Tam, J. P., Proc. Natl. Acad. Sci. USA, 85, 5409–5413 (1988)], and can be used for immunization in the same manner as above.

It is also possible to prepare a monoclonal antibody by a conventional method [Cell & Tissue Culture; Laboratory Procedure (Doyle, A. et al., eds.) 25A: 1–25C: 4, John Wiley & Sons, New York (1994)] using a polypeptide containing the entire or portion of human or rat ORP150 as an antigen. Specifically, a hybridoma is prepared by fusing mouse splenocytes immunized with said antigen and a myeloma cell line, and the resulting hybridoma is cultured or intraperitoneally transplanted to the mouse to produce a monoclonal antibody.

The fragments resulting from protease digestion of these antibodies as purified can also be used as antibodies of the present invention.

EXAMPLES

The following examples illustrate the present invention but are not intended to limit the invention in any manner.

Example 1
Cell Culture and Achievement of Hypoxic Condition

Rat primary astrocytes and microglia were obtained from neonatal rats by a modification of a previously described method [Maeda, Y., Matsumoto, M., Ohtsuki, T., Kuwabara, K., Ogawa, S., Hori, O., Shui; D. Y., Kinoshita, T., Kamada, T., and Stern, D., J. Exp. Med., 180, 2297–2308(1994)]. Briefly, cerebral hemispheres were harvested from neonatal Sprague-Dawley rats within 24 hours after birth, meninges were carefully removed, and brain tissue was digested at 37° C. in minimal essential medium (MEM) with Joklik's modification (Gibco, Boston Mass.) containing Dispase II (3 mg/ml; Boehringer-Mannheim, Germany). After centrifugation, the cell pellet was resuspended and grown in MEM supplemented with fetal calf serum (FCS; 10%; CellGrow, Mass.).

After 10 days, cytosine arabinofuranoside (10 $\mu$g/ml; Wako Chemicals, Osaka, Japan) was added for 48 hours to prevent fibroblast overgrowth, and culture flasks were agitated on a shaking platform. Then, floating cells were aspirated (these were microglia), and the adherent cell population was identified by morphological criteria and immunohistochemical staining with anti-glial fibrillary acidic protein antibody. Cultures used for experiments were >98% astrocytes based on these techniques.

Human astrocytoma cell line U373 was obtained from American Type Culture Collection (ATCC) and cultured in Dulbecco's modified Eagle medium (produced by Life Technology) supplemented with 10% FCS.

Cells were plated at a density of about $5 \times 10^4$ cells /cm$^2$ in the above medium. When cultures achieved confluence, they were exposed to hypoxia using an incubator attached to a hypoxia chamber which maintained a humidified atmosphere with low oxygen tension (Coy Laboratory Products, Ann Arbor Mich.) as described previously [Ogawa, S., Gerlach, H., Esposito, C., Macaulay, A. P., Brett, J., and Stern, D., J. Clin. Invest., 85, 1090–1098 (1990)].

Example 2
Purification and N-terminal Sequencing of the Rat 150 kDa Polypeptide Rat primary astrocytes (about $5 \times 10^8$ cells) exposed to hypoxia for 48 hours were harvested, cells were washed three times with PBS(pH 7.0) and protein was extracted with PBS containing NP-40 (1%), PMSF (1 mM), and EDTA (5 mM). Extracts were then filtered (0.45 $\mu$m nitrocellulose membrane), and either subjected to reduced SDS-PAGE (7.5%, about 25 $\mu$g) or 2–3 mg of protein was diluted with 50 ml of PBS (pH 7.0) containing NP-40(0.05%) and EDTA (5 mM), and applied to FPLC Mono Q(bed volume 5 ml, Pharmacia, Sweden).

The column was washed with 0.2M NaCl, eluted with an ascending salt gradient (0.2 to 1.8 M NaCl) and 10 $\mu$l of each fraction (0.5 ml) was applied to reduced SDS-PAGE (7.5%), along with molecular weight markers (Biorad). Proteins in the gel were visualized by silver staining. Fractions eluted from FPLC Mono Q which contained the 150 kDa polypeptide (#7–8) were pooled and concentrated by ultrafiltration (Amicon) 50-fold and about 200 $\mu$g of protein was applied to preparative, reduced SDS-PAGE (7.5%). Following electrophoresis, proteins in the gel were transferred electrophoretically (2A/cm$^2$) to polyvinylidene difluoride (PVDF) paper (Millipore, Tokyo), the paper was dried, stained with Coomassie Brilliant blue, and the band corresponding to 150 kDa protein (OPR150) was cut out for N-terminal sequencing using an automated peptide sequencing system (Applied Biosystems, Perkin-Elmer). The N-terminal 31-amino acid sequence was thus determined (SEQ ID NO:5).

Example 3
Preparation of Rat Astrocyte cDNA Library

Total RNA was prepared from rat primary astrocytes ($1.1 \times 10^8$ cells), in which ORP150 had been induced under hypoxic conditions, by the acid guanidinium-phenol-chloroform method [Chomczynski, P. and Sacchi, N., Anal. Biochem., 162, 156–159 (1987)]. Using 300 $\mu$g of the total RNA obtained, purification was conducted twice in accordance with the protocol for poly(A)$^+$ RNA purification using oligo(dT)-magnetic beads (produced by Perceptive Diagnostics), to yield poly(A)$^+$ RNA. Double-stranded cDNA was then synthesized using random hexamer primers, in accordance with the protocol for the Superscript Choice System (produced by Life Technology), and inserted into the EcoRI site of the pSPORT1 vector to prepare a cDNA library consisting of $5.4 \times 10^5$ independent clones.

Example 4
Cloning of Rat ORP150 cDNA

Rat ORP150 cDNA was cloned as follows: First, to obtain a probe for colony hybridization, the cDNA library was subjected to PCR using a 20-base primer, 5'-AATACGACTCACTATAGGGA-3' (SEQ ID NO:6), which corresponds to the antisense strand of the T7 promoter region in the pSPORT1 vector, and 20 base mixed primers, 5'-AARCCiGGiGTNCCNATGGA-3'(SEQ ID NO:8), which contains inosine residues and degenerate polynucleotides and which was prepared on the basis of the oligonucleotide sequence deduced from a partial sequence (KPGVPME) (SEQ ID NO:7) within the N-terminal amino acid sequence (LAVMSVDLGSESMKVAIVKPGVPMEIVLNKE) (SEQ ID NO:5); the resulting PCR product with a length of about 480 bp was inserted into the pT7 Blue Plasmid vector. Nucleotide sequences of the clones containing an insert of the expected size (480 bp) corresponding to the PCR product were determined using an automatic nucleotide sequencer (produced by Perkin-Elmer, Applied Biosystems). A clone containing a 39-nucleotide sequence encoding a peptide identical to the rat ORP150-specific amino acid sequence KPGVPMEIVLNKE (SEQ ID NO:9) in the insert was thus obtained.

Using the above insert of the clone as a probe, RNA from cultured rat astrocytes were subjected to Northern blotting; the results demonstrated that mRNA with a length of about 4 Kb was induced by hypoxic treatment. Thereupon, the above insert of the clone was labeled by the random prime labeling method (Ready TOGO, produced by Pharmacia) using $\alpha$-[$^{32}$P]dCTP to yield a probe. Using this probe, $1.2 \times 10^4$ clones of the cDNA library were screened by colony hybridization to obtain a clone containing a 2800 bp insert. The nucleotide sequence of this clone insert was determined by preparing deletion mutants using a kilosequence deletion kit (produced by Takara Shuzo).

Since this clone did not contain the 3'-region of the ORP150 coding sequence, the following two 20-base oligonucleotides were prepared on the basis of the specific nucleotide sequence near the 3' end of the above insert, to obtain the full-length sequence.
5'-GCACCCTTGAGGAAAATGCT-3' (SEQ ID NO:10)
5'-CCCAGAAGCCCAATGAGAAG-3' (SEQ ID NO:11)

Using the two oligonucleotides, a clone containing the entire coding region was selected from the rat astrocyte cDNA library in accordance with the protocol for the Gene Trapper cDNA Positive Selection System (produced by Life Technology), and its nucleotide sequence was determined.

The nucleotide sequence of rat ORP150 cDNA was thus determined as shown by SEQ ID NO:4 in the sequence listing. Based on this nucleotide sequence, the amino acid sequence of rat ORP150 was determined as shown by SEQ ID NO:3 in the sequence listing.

Example 5
Preparation of Human U373 cDNA Library

Poly(A)+ RNA was purified from U373 cells (1×10$^8$ cells) in which human ORP150 had been induced under hypoxic conditions, in the same manner as described in Example 3. Double-stranded cDNA was then synthesized in accordance with the protocol for the Superscript Choice System (produced by Life Technology) using a 1:1 mixture of random hexamer primers and an oligo(dT) primer. This cDNA was inserted into the EcoRI site of the pSPORT1 vector to prepare a cDNA library consisting of 2×10$^5$ independent clones.

Specifically, the library was prepared as follows:

Human U373 cells, cultured in 10 plastic petri dishes (150 mm in diameter)(1×10$^7$ cells/dish), were subjected to hypoxic treatment for 48 hours by the method of Ogawa et al. [Ogawa, S., Gerlach, H., Esposito, C., Mucaulay, A. P., Brett, J., and Stern, D., J. Clin. Invest., 85, 1090–1098 (1990)] as described in Example 3, after which total RNA was prepared by the acid guanidinium-phenol-chloroform method [Chomczynski, P. and Sacchi, N., Anal. Biochem., 162, 156–159 (1987)]. Using 500 μg of the total RNA obtained, purification was conducted twice in accordance with the protocol for poly(A)+ RNA purification using oligo(dT)-magnetic beads (produced by Perceptive Diagnostics), to yield poly(A)+ RNA. Double-stranded cDNA was then synthesized using 5 μg of the poly(A)+ RNA and a 1:1 mixture of random hexamer primers and an oligo(dT) primer, in accordance with the protocol for the Superscript Choice System (produced by Life Technology), and inserted into the EcoRI site of the pSPORT1 vector to prepare a human U373 cDNA library consisting of 2×10$^5$ independent clones.

Example 6
Cloning of Human ORP150 cDNA

Using two primers (SEQ ID NO:10 and SEQ ID NO:11) prepared on the basis of the above-described rat ORP150 cDNA specific sequence, a clone containing the entire coding region was selected from the human U373 cDNA library in accordance with the protocol for the Gene Trapper cDNA Positive Selection System (produced by Life Technology), and its nucleotide sequence was determined. The nucleotide sequence of human ORP150 cDNA was thus determined as shown by SEQ ID NO:2 in the sequence listing.

Specifically, 2×10$^4$ clones of the human U373 cDNA library were amplified in accordance with the protocol for the Gene Trapper cDNA Positive Selection System (produced by Life Technology). Five micrograms of the plasmid purified from amplified clones were treated with the Gene II and Exo III nuclease included in the kit to yield single-stranded DNA. An oligonucleotide (SEQ ID NO:10) prepared on the basis of the above-described rat ORP150 cDNA-specific sequence was biotinylated and subsequently hybridized to the above single-stranded DNA at 37° C. for 1 hour. The single-stranded DNA hybridized to the oligonucleotide derived from rat ORP150 cDNA was selectively recovered by using streptoavidin-magnetic beads, and was treated with the repair enzyme included in the kit using the oligonucleotide shown by SEQ ID NO:10 in the sequence listing as a primer, to yield double-stranded plasmid DNA.

The double-stranded plasmid DNA was then introduced to ElectroMax DH10B cells (produced by Life Technology) in accordance with the protocol for the Gene Trapper cDNA Positive Selection System, followed by colony PCR in accordance with the same protocol using two primers (SEQ ID NO:10 and SEQ ID NO:11) prepared on the basis of the rat ORP150 cDNA-specific sequence, to select clones that yield an about 550 bp PCR product. The nucleotide sequence of the longest insert among these clones, corresponding to the human ORP150 cDNA, was determined as shown by SEQ ID NO:2 in the sequence listing.

On the basis of this nucleotide sequence, the amino acid sequence of human ORP150 was determined as shown by SEQ ID NO:1 in the sequence listing.

The N-terminal amino acid sequence (SEQ ID NO:5) obtained with purified rat ORP150 corresponded to amino acids 33–63 deduced from both the human and rat cDNAs, indicating that the first 32 residues represent the signal peptides for secretion. The C-terminal KNDEL sequence, which resembles KDEL sequence, a signal to retain the ER-resident proteins [Pelham, H. R. B., Trends Biochem. Sci. 15, 483–486 (1990)], may function as an ER-retention signal. The existence of a signal peptide at the N-terminus and the ER-retention signal-like sequence at the C-terminus suggests that ORP150 resides in the ER, consistent with the results of immunocytochemical analysis reported by Kuwabara et al. [Kuwabara, K., Matsumoto, M., Ikeda, J., Hori, O., Ogawa, S., Maeda, Y., Kitagawa, K., Imuta, N., Kinoshita, T., Stern, D. M., Yanagi, H., and Kamada, T., J. Biol. Chem. 271, 5025–5032 (1996)].

Analysis of protein data bases with the BLAST program [Altschul, S. F., Gish, W., Miller, W., Myers, E. W., and Lipman, D. J., J. Mol., Biol. 215, 403–410(1990)] showed that the N-terminal half of ORP150 has a modest similarity to the ATPase domain of numerous HSP70 family sequences. An extensive analysis with pairwise alignments [Pearson, W. R., and Lipman, D. J., Proc. Natl. Acad. Sci. USA 85, 2444–2448(1988)] revealed that amino acids 33–426 of human ORP150 was 32% identical to amino acids 1–380 of both inducible human HSP70.1 [Hunt, C., and Morimoto, R. I., Proc. Natl. Acad. Sci. USA 82, 6455–6459 (1985)] and constitutive bovine HSC70 [DeLuca-Flaherty, C., and McKay, D. B., Nucleic Acids Res. 18, 5569(1990)], typical members of HSP70 family. An additional region similar to HSP70RY and hamster HSP110, which both belong to a new subfamily of large HSP70-like proteins [Lee-Yoon, D., Easton, D., Murawski, M., Burd, R., and Subjeck, J. R., J. Biol. Chem. 270, 15725–15733 (1995)], extended further to residue 487. A protein sequence motif search with PROSITE [Bairoch, A., and Bucher, P., Nucleic Acids Res. 22, 3583–3589(1994)] showed that ORP150 contains two of the three HSP70 protein family signatures: FYDMGSGSTVCTIV (amino acids 230–243, SEQ ID NO:1) and VILVGGATRVPRVQE (amino acids 380–394, SEQ ID NO:1) which completely matched with the HSP70 signatures 2 and 3, respectively, and VDLG (amino acids 38–41, SEQ ID NO:1) which matched with the first four amino acids of the signature 1. Furthermore, the N-terminal region of ORP150 contained a putative ATP-binding site consisting of the regions (amino acids 36–53, 197–214, 229–243, 378–400, and 411–425, SEQ ID NO:1) corresponding to the five motifs specified by Bork et al. [Bork, P., Sander, C., and Valencia, A., Proc. Natl. Acad. Sci. USA 89, 7290–7294 (1992)]. Although the C-terminal putative peptide-binding domains of HSP70 family are generally less conserved [Rippmann, F., Taylor, W. R., Rothbard, J. B., and Green, N. M., EMBO J. 10, 1053–1059 (1991)], the C-terminal region flanked by amino acids 701 and 898 (SEQ ID NO:1) shared appreciable similarity with HSP110 (amino acids 595–793 SEQ ID NO:1; 29% identity).

Example 7
Cloning of Human ORP150 Genomic DNA

A human genomic library purchased from Clontech (derived from human placenta, Cat. #HL1067J, Lot #1221, 2.5×10$^6$ independent clones) was used. A DNA fragment consisting of 202 bp of the 5' untranslated region and 369 bp of the coding region derived from the rat cDNA clone, as well as a 1351 bp DNA fragment containing the termination codon, derived from the human cDNA, were used as probes for plaque hybridization.

*Escherichia coli* LE392, previously infected with 1×10$^6$ pfu of the human genomic library, was plated onto 10 petri dishes 15 cm in diameter to allow plaque formation. The phage DNA was transferred to a nylon membrane (Hybond-N$^+$, Amersham) and denatured with sodium hydroxide, after which it was fixed by ultraviolet irradiation. The rat cDNA probe was labeled using a DNA labeling kit (Ready To Go, Pharmacia), and hybridized with the membrane in the Rapid-hyb buffer (Amersham). After incubation at 65° C. for 2 hours, the nylon membrane was washed with 0.2×SSC-0.1% SDS, and a positive clone was detected on an imaging plate (Fuji Photo Film). Since the clone isolated contained only exons 1 through 24, 1.5×10$^6$ clones of the same library was screened again using the human cDNA probe in the same manner, resulting in isolation of one clone. This clone was found to contain exons 16 through 26, with an overlap with the 3' region of the above-mentioned clone. The entire region of the ORP150 gene was thus cloned by combining these two clones.

These two clones were cleaved with BamHI and subcloned into pBluescript IISK (Stratagene), followed by nucleotide sequence determination of the entire 15851 bp human ORP150 genomic DNA. The nucleotide sequence from the 5' end to just before the translation initiation codon ATG in exon 2 is shown by SEQ ID NO:12 in the sequence listing.

Furthermore, the nucleotide sequence of the 15851 bp human ORP150 genomic DNA was compared with that of the human ORP150 cDNA shown by SEQ ID NO:2 in the sequence listing, resulting in the demonstration of the presence of the exons at the positions shown below. A schematic diagram of the positions of the exons is shown in FIG. 1.

|  |  | (Base position in SEQ ID:2) |
|---|---|---|
| Exon 1 | 1908–2002 | (1–95) |
| Exon 2 | 2855–2952 | (96–193) |
| Exon 3 | 3179–3272 | (194–287) |
| Exon 4 | 3451–3529 | (288–366) |
| Exon 5 | 3683–3837 | (367–521) |
| Exon 6 | 3962–4038 | (522–598) |
| Exon 7 | 4347–4528 | (599–780) |
| Exon 8 | 4786–4901 | (781–896) |
| Exon 9 | 6193–6385 | (897–1089) |
| Exon 10 | 6593–6727 | (1090–1224) |
| Exon 11 | 6850–6932 | (1225–1307) |
| Exon 12 | 7071–7203 | (1308–1440) |
| Exon 13 | 7397–7584 | (1441–1628) |
| Exon 14 | 7849–7987 | (1629–1767) |
| Exon 15 | 9176–9236 | (1768–1828) |
| Exon 16 | 9378–9457 | (1829–1908) |
| Exon 17 | 9810–9995 | (1209–2094) |
| Exon 18 | 10127–10299 | (2095–2267) |
| Exon 19 | 10450–10537 | (2268–2355) |
| Exon 20 | 10643–10765 | (2356–2478) |
| Exon 21 | 10933–11066 | (2479–2612) |

-continued

|  |  | (Base position in SEQ ID:2) |
|---|---|---|
| Exon 22 | 11195–11279 | (2613–2697) |
| Exon 23 | 12211–12451 | (2698–2938) |
| Exon 24 | 12546–12596 | (2939–2989) |
| Exon 25 | 13181–13231 | (2990–3040) |
| Exon 26 | 13358–14823 | (3041–4503) |

Example 8

Northern Blot Analysis

A 4.5-kb EcoRI fragment of human ORP150 cDNA was labeled with [α-$^{32}$P]dCTP(3,000 Ci/mmol; Amersham Corp., Arlington Heights, Ill.) by using a DNA labeling kit (Pharmacia), and used as a hybridization probe. 20 μg of total RNA prepared from U373 cells exposed to various stresses were electrophoresed and transferred onto a Hybond N$^+$ membrane (Amersham Corp.). Multiple Tissue Northern Blots, in which each lane contained 2 μg of poly(A)RNA from the adult human tissues indicated, was purchased from Clontech. The filter was hybridized at 65° C. in the Rapid-hyb buffer (Amersham Corp.) with human ORP150, GRP78, HSP70, glyceraldehyde-3-phosphate dehydrogenase (G3PDH), and β-actin cDNAs each labeled with [α$^{32}$-P] dCTP, washed with 0.1×SSC containing 0.1% SDS at 65° C., and followed by autoradiography.

Figure 2:
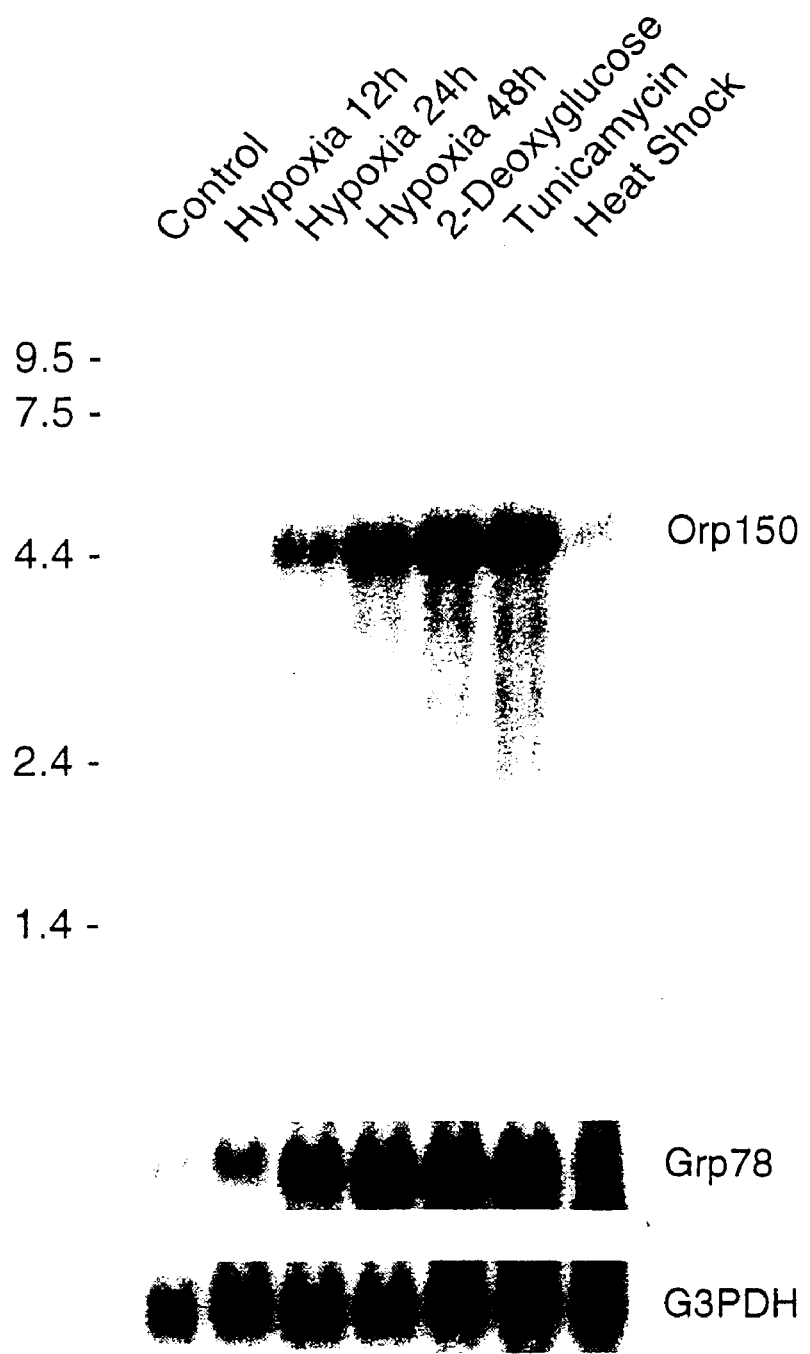
FIG. 2 shows the results of the Northern blot analysis of ORP150 mRNA extracted from human astrocytoma U373 cells after exposure to various types of stress.

As shown in FIG. 2, the ORP150 mRNA level was highly enhanced upon 24–48 hours of exposure to hypoxia. In parallel experiments, treatment with 2-deoxyglucose (25 mM, 24 hours) or tunicamycin (5 μg/ml, 24 hours) enhanced ORP150 mRNA to the levels comparable to that induced by hypoxia. The induction levels were also comparable with those observed for mRNA of a typical glucose-regulated protein GRP78. Heat shock treatment failed to enhance ORP150 mRNA appreciably.

Figure 3:
FIG. 3 shows the results of the Northern blot analysis of ORP150 mRNA from adult human tissues.

ORP150 mRNA was found to be highly expressed in the liver and pancreas, whereas little expression was observed in kidney and brain (FIG. 3). Furthermore, the tissue specificity of ORP150 expression was quite similar to that of GRP78. The higher expression observed in the tissues that contain well-developed ER and synthesize large amounts of secretory proteins is consistent with the finding that ORP150 is localized in the ER (Kuwabara, K., Matsumoto, M., Ikeda, J., Hori, O., Ogawa, S., Maeda, Y., Kitagawa, K., Imuta, N., Kinoshita, T., Stern, D. M., Yanagi, H., and Kamada, T., J. Biol. Chem. 271, 5025–5032(1996)).

In conclusion, both the characteristic primary protein structure and the similarity found with GRP78 in stress inducibility and tissue specificity suggest that ORP150 plays an important role in protein folding and secretion in the ER, perhaps as a molecular chaperone, in concert with other GRPs to cope with environmental stress.

Those skilled in the art will recognize, or be able to ascertain using no more than routine experimentation, many equivalents to the specific embodiments of the present invention described specifically herein. Such equivalents are intended to be encompassed in the scope of the following claims.

What is claimed is:

1. A polynucleotide which hybridizes to a polynucleotide consisting of the nucleotide sequence of SEQ ID NO:12 and is capable of promoting the expression of a polypeptide of SEQ ID NO:2.

2. An isolated rat or human polynucleotide which hybridizes to a polynucleotide having a sequence of SEQ ID NO:12, in 0.1×SSC containing 0.1% SDS at 65° C. and which has promoter activity under hypoxia conditions and is associated with a coding sequence of a native rat or human gene encoding a 150 kD hypoxia-induced stress protein.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 999 amino acids
        (B) TYPE:  amino acid
        (D) TOPOLOGY: linear (ii) MOLECULE TYPE: peptide (xi) SEQUENCE DESCRIPTION:    SEQ ID NO:1:

```
Met Ala Asp Lys Val Arg Arg Gln Arg Pro Arg Arg Val Cys Trp
                 5                  10                  15

Ala Leu Val Ala Val Leu Leu Ala Asp Leu Leu Ala Leu Ser Asp Thr
             20                  25                  30

Leu Ala Val Met Ser Val Asp Leu Gly Ser Glu Ser Met Lys Val Ala
             35                  40                  45

Ile Val Lys Pro Gly Val Pro Met Glu Ile Val Leu Asn Lys Glu Ser
 50                  55                  60

Arg Arg Lys Thr Pro Val Ile Val Thr Leu Lys Glu Asn Glu Arg Phe
 65                  70                  75                  80

Phe Gly Asp Ser Ala Ala Ser Met Ala Ile Lys Asn Pro Lys Ala Thr
                 85                  90                  95

Leu Arg Tyr Phe Gln His Leu Leu Gly Lys Gln Ala Asp Asn Pro His
                100                 105                 110

Val Ala Leu Tyr Gln Ala Arg Phe Pro Glu His Glu Leu Thr Phe Asp
            115                 120                 125

Pro Gln Arg Gln Thr Val His Phe Gln Ile Ser Ser Gln Leu Gln Phe
130                 135                 140

Ser Pro Glu Glu Val Leu Gly Met Val Leu Asn Tyr Ser Arg Ser Leu
145                 150                 155                 160

Ala Glu Asp Phe Ala Glu Gln Pro Ile Lys Asp Ala Val Ile Thr Val
                165                 170                 175

Pro Val Phe Phe Asn Gln Ala Glu Arg Arg Ala Val Leu Gln Ala Ala
            180                 185                 190

Arg Met Ala Gly Leu Lys Val Leu Gln Leu Ile Asn Asp Asn Thr Ala
            195                 200                 205

Thr Ala Leu Ser Tyr Gly Val Phe Arg Arg Lys Asp Ile Asn Thr Thr
210                 215                 220

Ala Gln Asn Ile Met Phe Tyr Asp Met Gly Ser Gly Ser Thr Val Cys
225                 230                 235                 240

Thr Ile Val Thr Tyr Gln Met Val Lys Thr Lys Glu Ala Gly Met Gln
                245                 250                 255

Pro Gln Leu Gln Ile Arg Gly Val Gly Phe Asp Arg Thr Leu Gly Gly
            260                 265                 270

Leu Glu Met Glu Leu Arg Leu Arg Glu Arg Leu Ala Gly Leu Phe Asn
            275                 280                 285

Glu Gln Arg Lys Gly Gln Arg Ala Lys Asp Val Arg Glu Asn Pro Arg
290                 295                 300

Ala Met Ala Lys Leu Leu Arg Glu Ala Asn Arg Leu Lys Thr Val Leu
305                 310                 315                 320

Ser Ala Asn Ala Asp His Met Ala Gln Ile Glu Gly Leu Met Asp Asp
                325                 330                 335

Val Asp Phe Lys Ala Lys Val Thr Arg Val Glu Phe Glu Glu Leu Cys
            340                 345                 350
```

-continued

```
Ala Asp Leu Phe Glu Arg Val Pro Gly Pro Val Gln Gln Ala Leu Gln
        355                 360                 365

Ser Ala Glu Met Ser Leu Asp Glu Ile Glu Gln Val Ile Leu Val Gly
        370                 375                 380

Gly Ala Thr Arg Val Pro Arg Val Gln Glu Val Leu Leu Lys Ala Val
385                 390                 395                 400

Gly Lys Glu Glu Leu Gly Lys Asn Ile Asn Ala Asp Glu Ala Ala Ala
                405                 410                 415

Met Gly Ala Val Tyr Gln Ala Ala Leu Ser Lys Ala Phe Lys Val
                420                 425                 430

Lys Pro Phe Val Val Arg Asp Ala Val Val Tyr Pro Ile Leu Val Glu
        435                 440                 445

Phe Thr Arg Glu Val Glu Glu Pro Gly Ile His Ser Leu Lys His
        450                 455                 460

Asn Lys Arg Val Leu Phe Ser Arg Met Gly Pro Tyr Pro Gln Arg Lys
465                 470                 475                 480

Val Ile Thr Phe Asn Arg Tyr Ser His Asp Phe Asn Phe His Ile Asn
                485                 490                 495

Tyr Gly Asp Leu Gly Phe Leu Gly Pro Glu Asp Leu Arg Val Phe Gly
                500                 505                 510

Ser Gln Asn Leu Thr Thr Val Lys Leu Lys Gly Val Gly Asp Ser Phe
        515                 520                 525

Lys Lys Tyr Pro Asp Tyr Glu Ser Lys Gly Ile Lys Ala His Phe Asn
        530                 535                 540

Leu Asp Glu Ser Gly Val Leu Ser Leu Asp Arg Val Glu Ser Val Phe
545                 550                 555                 560

Glu Thr Leu Val Glu Asp Ser Ala Glu Glu Ser Thr Leu Thr Lys
                565                 570                 575

Leu Gly Asn Thr Ile Ser Ser Leu Phe Gly Gly Thr Thr Pro Asp
        580                 585                 590

Ala Lys Glu Asn Gly Thr Asp Thr Val Gln Glu Glu Glu Ser Pro
        595                 600                 605

Ala Glu Gly Ser Lys Asp Glu Pro Gly Glu Gln Val Glu Leu Lys Glu
610                 615                 620

Glu Ala Glu Ala Pro Val Glu Asp Gly Ser Gln Pro Pro Pro Glu
625                 630                 635                 640

Pro Lys Gly Asp Ala Thr Pro Glu Gly Glu Lys Ala Thr Glu Lys Glu
                645                 650                 655

Asn Gly Asp Lys Ser Glu Ala Gln Lys Pro Ser Glu Lys Ala Glu Ala
                660                 665                 670

Gly Pro Glu Gly Val Ala Pro Pro Glu Gly Glu Lys Lys Gln Lys
                675                 680                 685

Pro Ala Arg Lys Arg Arg Met Val Glu Glu Ile Gly Val Glu Leu Val
        690                 695                 700

Val Leu Asp Leu Pro Asp Leu Pro Glu Asp Lys Leu Ala Gln Ser Val
705                 710                 715                 720

Gln Lys Leu Gln Asp Leu Thr Leu Arg Asp Leu Glu Lys Gln Glu Arg
                725                 730                 735

Glu Lys Ala Ala Asn Ser Leu Glu Ala Phe Ile Phe Glu Thr Gln Asp
                740                 745                 750

Lys Leu Tyr Gln Pro Glu Tyr Gln Glu Val Ser Thr Glu Gln Arg
        755                 760                 765

Glu Glu Ile Ser Gly Lys Leu Ser Ala Ala Ser Thr Trp Leu Glu Asp
```

```
              770            775             780
Glu Gly Val Gly Ala Thr Thr Val Met Leu Lys Glu Lys Leu Ala Glu
785                 790                795                 800

Leu Arg Lys Leu Cys Gln Gly Leu Phe Phe Arg Val Glu Glu Arg Lys
                805                 810                 815

Lys Trp Pro Glu Arg Leu Ser Ala Leu Asp Asn Leu Leu Asn His Ser
            820                 825                 830

Ser Met Phe Leu Lys Gly Ala Arg Leu Ile Pro Glu Met Asp Gln Ile
            835                 840                 845

Phe Thr Glu Val Glu Met Thr Thr Leu Glu Lys Val Ile Asn Glu Thr
        850                 855                 860

Trp Ala Trp Lys Asn Ala Thr Leu Ala Glu Gln Ala Lys Leu Pro Ala
865                 870                 875                 880

Thr Glu Lys Pro Val Leu Leu Ser Lys Asp Ile Glu Ala Lys Met Met
                885                 890                 895

Ala Leu Asp Arg Glu Val Gln Tyr Leu Leu Asn Lys Ala Lys Phe Thr
                900                 905                 910

Lys Pro Arg Pro Arg Pro Lys Asp Lys Asn Gly Thr Arg Ala Glu Pro
            915                 920                 925

Pro Leu Asn Ala Ser Ala Ser Asp Gln Gly Glu Lys Val Ile Pro Pro
930                 935                 940

Ala Gly Gln Thr Glu Asp Ala Glu Pro Ile Ser Glu Pro Glu Lys Val
945                 950                 955                 960

Glu Thr Gly Ser Glu Pro Gly Asp Thr Glu Pro Leu Glu Leu Gly Gly
                965                 970                 975

Pro Gly Ala Glu Pro Glu Gln Lys Glu Gln Ser Thr Gly Gln Lys Arg
            980                 985                 990

Pro Leu Lys Asn Asp Glu Leu
        995

(2) INFORMATION FOR SEQ ID NO:2:

(i) SEQUENCE CHARACTERISTICS:
        (A) LENGTH: 4503 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) IDENTIFICATION METHOD: E (xi) SEQUENCE DESCRIPTION: SEQ ID NO:2:

TTGTGAAGGG CGCGGGTGGG GGGCGCTGCC GGCCTCGTGG GTACGTTCGT GCCGCGTCTG      60

TCCCAGAGCT GGGGCCGCAG GAGCGGAGGC AAGAGGGGCA CTATGGCAGA CAAAGTTAGG    120

AGGCAGAGGC CGAGGAGGCG AGTCTGTTGG GCCTTGGTGG CTGTGCTCTT GGCAGACCTG    180

TTGGCACTGA GTGATACACT GGCAGTGATG TCTGTGGACC TGGGCAGTGA GTCCATGAAG    240

GTGGCCATTG TCAAACCTGG AGTGCCCATG GAAATTGTCT TGAATAAGGA ATCTCGGAGG    300

AAAACACCGG TGATCGTGAC CCTGAAAGAA AATGAAAGAT TCTTTGGAGA CAGTGCAGCA    360

AGCATGGCGA TTAAGAATCC AAAGGCTACG CTACGTTACT TCCAGCACCT CCTGGGGAAG    420

CAGGCAGATA ACCCCCATGT AGCTCTTTAC CAGGCCCGCT TCCCGGAGCA CGAGCTGACT    480

TTCGACCCAC AGAGGCAGAC TGTGCACTTT CAGATCAGCT CGCAGCTGCA GTTCTCACCT    540
```

```
GAGGAAGTGT TGGGCATGGT TCTCAATTAT TCTCGTTCTC TAGCTGAAGA TTTTGCAGAG      600

CAGCCCATCA AGGATGCAGT GATCACCGTG CCAGTCTTCT TCAACCAGGC CGAGCGCCGA      660

GCTGTGCTGC AGGCTGCTCG TATGGCTGGC CTCAAAGTGC TGCAGCTCAT CAATGACAAC      720

ACCGCCACTG CCCTCAGCTA TGGTGTCTTC CGCCGGAAAG ATATTAACAC CACTGCCCAG      780

AATATCATGT TCTATGACAT GGGCTCAGGC AGCACCGTAT GCACCATTGT GACCTACCAG      840

ATGGTGAAGA CTAAGGAAGC TGGGATGCAG CCACAGCTGC AGATCCGGGG AGTAGGATTT      900

GACCGTACCC TGGGGGGCCT GGAGATGGAG CTCCGGCTTC GAGAACGCCT GGCTGGGCTT      960

TTCAATGAGC AGCGCAAGGG TCAGAGAGCA AAGGATGTGC GGGAGAACCC GCGTGCCATG     1020

GCCAAGCTGC TGCGTGAGGC TAATCGGCTC AAAACCGTCC TCAGTGCCAA CGCTGACCAC     1080

ATGGCACAGA TTGAAGGCCT GATGGATGAT GTGGACTTCA AGGCAAAAGT GACTCGTGTG     1140

GAATTTGAGG AGTTGTGTGC AGACTTGTTT GAGCGGGTGC CTGGGCCTGT ACAGCAGGCC     1200

CTCCAGAGTG CCGAAATGAG TCTGGATGAG ATTGAGCAGG TGATCCTGGT GGGTGGGGCC     1260

ACTCGGGTCC CCAGAGTTCA GGAGGTGCTG CTGAAGGCCG TGGGCAAGGA GGAGCTGGGG     1320

AAGAACATCA ATGCAGATGA AGCAGCCGCC ATGGGGGCAG TGTACCAGGC AGCTGCGCTC     1380

AGCAAAGCCT TTAAAGTGAA GCCATTTGTC GTCCGAGATG CAGTGGTCTA CCCCATCCTG     1440

GTGGAGTTCA CGAGGGAGGT GGAGGAGGAG CCTGGGATTC ACAGCCTGAA GCACAATAAA     1500

CGGGTACTCT TCTCTCGGAT GGGGCCCTAC CCTCAACGCA AAGTCATCAC CTTTAACCGC     1560

TACAGCCATG ATTTCAACTT CCACATCAAC TACGGCGACC TGGGCTTCCT GGGGCCTGAA     1620

GATCTTCGGG TATTTGGCTC CCAGAATCTG ACCACAGTGA AGCTAAAAGG GGTGGGTGAC     1680

AGCTTCAAGA AGTATCCTGA CTACGAGTCC AAGGGCATCA AGGCTCACTT CAACCTGGAT     1740

GAGAGTGGCG TGCTCAGTCT AGACAGGGTG GAGTCTGTAT TTGAGACACT GGTAGAGGAC     1800

AGCGCAGAAG AGGAATCTAC TCTCACCAAA CTTGGCAACA CCATTTCCAG CCTGTTTGGA     1860

GGCGGTACCA CACCAGATGC CAAGGAGAAT GGTACTGATA CTGTCCAGGA GGAAGAGGAG     1920

AGCCCTGCAG AGGGGAGCAA GGACGAGCCT GGGGAGCAGG TGGAGCTCAA GGAGGAAGCT     1980

GAGGCCCCAG TGGAGGATGG CTCTCAGCCC CCACCCCCTG AACCTAAGGG AGATGCAACC     2040

CCTGAGGGAG AAAAGGCCAC AGAAAAAGAA AATGGGGACA AGTCTGAGGC CCAGAAACCA     2100

AGTGAGAAGG CAGAGGCAGG GCCTGAGGGC GTCGCTCCAG CCCCAGAGGG AGAGAAGAAG     2160

CAGAAGCCCG CCAGGAAGCG GCGAATGGTA GAGGAGATCG GGGTGGAGCT GGTTGTTCTG     2220

GACCTGCCTG ACTTGCCAGA GGATAAGCTG GCTCAGTCGG TGCAGAAACT TCAGGACTTG     2280

ACACTCCGAG ACCTGGAGAA GCAGGAACGG GAAAAAGCTG CCAACAGCTT GGAAGCGTTC     2340

ATATTTGAGA CCCAGGACAA GCTGTACCAG CCCGAGTACC AGGAAGTGTC CACAGAGGAG     2400

CAGCGTGAGG AGATCTCTGG GAAGCTCAGC GCCGCATCCA CCTGGCTGGA GGATGAGGGT     2460

GTTGGAGCCA CCACAGTGAT GTTGAAGGAG AAGCTGGCTG AGCTGAGGAA GCTGTGCCAA     2520

GGGCTGTTTT TCGGGTAGA GGAGCGCAAG AAGTGGCCCG AACGGCTGTC TGCCCTCGAT     2580

AATCTCCTCA ACCATTCCAG CATGTTCCTC AAGGGGCCC GGCTCATCCC AGAGATGGAC     2640

CAGATCTTCA CTGAGGTGGA GATGACAACG TTAGAGAAAG TCATCAATGA GACCTGGGCC     2700

TGGAAGAATG CAACTCTGGC CGAGCAGGCT AAGCTGCCCG CCACAGAGAA GCCTGTGTTG     2760

CTCTCAAAAG ACATTGAAGC TAAGATGATG GCCCTGGACC GAGAGGTGCA GTATCTGCTC     2820

AATAAGGCCA AGTTTACCAA GCCCCGGCCC CGGCCTAAGG ACAAGAATGG GACCCGGGCA     2880

GAGCCACCCC TCAATGCCAG TGCCAGTGAC CAGGGGGAGA AGGTCATCCC TCCAGCAGGC     2940
```

```
CAGACTGAAG ATGCAGAGCC CATTTCAGAA CCTGAGAAAG TAGAGACTGG ATCCGAGCCA    3000

GGAGACACTG AGCCTTTGGA GTTAGGAGGT CCTGGAGCAG AACCTGAACA GAAAGAACAA    3060

TCGACAGGAC AGAAGCGGCC TTTGAAGAAC GACGAACTAT AACCCCCACC TCTGTTTTCC    3120

CCATTCATCT CCACCCCCTT CCCCCACCAC TTCTATTTAT TTAACATCGA GGGTTGGGGG    3180

AGGGGTTGGT CCTGCCCTCG GCTGGAGTTC CTTTCTCACC CCTGTGATTT GGAGGTGTGG    3240

AGAAGGGGAA GGGAGGGACA GCTCACTGGT TCCTTCTGCA GTACCTCTGT GGTTAAAAAT    3300

GGAAACTGTT CTCCTCCCCA GCCCCACTCC CTGTTCCCTA CCCATATAGG CCCTAAATTT    3360

GGGAAAAATC ACTATTAATT TCTGAATCCT TTGCCTGTGG GTAGGAAGAG AATGGCTGCC    3420

AGTGGCTGAT GGGTCCCGGT GATGGGAAGG GTATCAGGTT GCTGGGGAGT TTCCACTCTT    3480

CTCTGGTGAT TGTTCCTTCC CTCCCTTCCT CTCCCACCAT GCGATGAGCA TCCTTTCAGG    3540

CCAGTGTCTG CAGAGCCTCA GTTACCAGGT TTGGTTTCTG AGTGCCTATC TGTGCTCTTT    3600

CCTCCCTCTG CGGGCTTCTC TTGCTCTGAG CCTCCCTTCC CCATTCCCAT GCAGCTCCTT    3660

TCCCCCTGGG TTTCCTTGGC TTCCTGCAGC AAATTGGGCA GTTCTCTGCC CCTTGCCTAA    3720

AAGCCTGTAC CTCTGGATTG GCGGAAGTAA ATCTGGAAGG ATTCTCACTC GTATTTCCCA    3780

CCCCTAGTGG CCAGAGGAGG GAGGGGCACA GTGAAGAAGG GAGCCCACCA CCTCTCCGAA    3840

GAGGAAAGCC ACGTAGAGTG GTTGGCATGG GGTGCCAGCA TCGTGCAAGC TCTGTCATAA    3900

TCTGCATCTT CCCAGCAGCC TGGTACCCCA GGTTCCTGTA ACTCCCTGCC TCCTCCTCTC    3960

TTCTGCTGTT CTGCTCCTCC CAGACAGAGC CTTTCCCTCA CCCCCTGACC CCCTGGGCTG    4020

ACCAAAATGT GCTTTCTACT GTGAGTCCCT ATCCCAAGAT CCTGGGGAAA GGAGAGACCA    4080

TGGTGTGAAT GTAGAGATGC CACCTCCCTC TCTCTGAGGC AGGCCTGTGG ATGAAGGAGG    4140

AGGGTCAGGG CTGGCCTTCC TCTGTGCATC ACTCTGCTAG GTTGGGGGCC CCCGACCCAC    4200

CATACCTACG CCTAGGGAGC CCGTCCTCCA GTATTCCGTC TGTAGCAGGA GCTAGGGCTG    4260

CTGCCTCAGC TCCAAGACAA GAATGAACCT GGCTGTTGCA GTCATTTTGT CTTTTCCTTT    4320

TTTTTTTTTT GCCACATTGG CAGAGATGGG ACCTAAGGGT CCCACCCCTC ACCCCACCCC    4380

CACCTCTTCT GTATGTTTGA ATTCTTTCAG TAGCTGTTGA TGCTGGTTGG ACAGGTTTGA    4440

GTCAAATTGT ACTTTGCTCC ATTGTTAATT GAGAAACTGT TCAATAAAA TATTCTTTTC     4500

TAC                                                                  4503
```

(2) INFORMATION FOR SEQ ID NO:3:

(i) SEQUENCE CHARACTERISTICS:
        (A) LENGTH: 999 amino acids
        (B) TYPE: amino acid
        (D) TOPOLOGY: linear (ii) MOLECULE TYPE: peptide (xi) SEQUENCE DESCRIPTION: SEQ ID NO:3:

```
Met Ala Ala Thr Val Arg Arg Gln Arg Pro Arg Arg Leu Leu Cys Trp
              5                  10                  15

Ala Leu Val Ala Val Leu Leu Ala Asp Leu Leu Ala Leu Ser Asp Thr
             20                  25                  30

Leu Ala Val Met Ser Val Asp Leu Gly Ser Glu Ser Met Lys Val Ala
         35                  40                  45

Ile Val Lys Pro Gly Val Pro Met Glu Ile Val Leu Asn Lys Glu Ser
    50                  55                  60
```

-continued

```
Arg Arg Lys Thr Pro Val Thr Val Thr Leu Lys Glu Asn Glu Arg Phe
65                  70                  75                  80

Leu Gly Asp Ser Ala Ala Gly Met Ala Ile Lys Asn Pro Lys Ala Thr
                85                  90                  95

Leu Arg Tyr Phe Gln His Leu Leu Gly Lys Gln Ala Asp Asn Pro His
            100                 105                 110

Val Ala Leu Tyr Arg Ser Arg Phe Pro Glu His Glu Leu Asn Val Asp
            115                 120                 125

Pro Gln Arg Gln Thr Val Arg Phe Gln Ile Ser Pro Gln Leu Gln Phe
130                 135                 140

Ser Pro Glu Glu Val Leu Gly Met Val Leu Asn Tyr Ser Arg Ser Leu
145                 150                 155                 160

Ala Glu Asp Phe Ala Glu Gln Pro Ile Lys Asp Ala Val Ile Thr Val
                165                 170                 175

Pro Ala Phe Phe Asn Gln Ala Glu Arg Arg Ala Val Leu Gln Ala Ala
                180                 185                 190

Arg Met Ala Gly Leu Lys Val Leu Gln Leu Ile Asn Asp Asn Thr Ala
            195                 200                 205

Thr Ala Leu Ser Tyr Gly Val Phe Arg Arg Lys Asp Ile Asn Ser Thr
            210                 215                 220

Ala Gln Asn Ile Met Phe Tyr Asp Met Gly Ser Gly Ser Thr Val Cys
225                 230                 235                 240

Thr Ile Val Thr Tyr Gln Thr Val Lys Thr Lys Glu Ala Gly Thr Gln
                245                 250                 255

Pro Gln Leu Gln Ile Arg Gly Val Gly Phe Asp Arg Thr Leu Gly Gly
                260                 265                 270

Leu Glu Met Glu Leu Arg Leu Arg Glu His Leu Ala Lys Leu Phe Asn
            275                 280                 285

Glu Gln Arg Lys Gly Gln Lys Ala Lys Asp Val Arg Glu Asn Pro Arg
290                 295                 300

Ala Met Ala Lys Leu Leu Arg Glu Ala Asn Arg Leu Lys Thr Val Leu
305                 310                 315                 320

Ser Ala Asn Ala Asp His Met Ala Gln Ile Glu Gly Leu Met Asp Asp
                325                 330                 335

Val Asp Phe Lys Ala Lys Val Thr Arg Val Glu Phe Glu Glu Leu Cys
                340                 345                 350

Ala Asp Leu Phe Asp Arg Val Pro Gly Pro Val Gln Gln Ala Leu Gln
            355                 360                 365

Ser Ala Glu Met Ser Leu Asp Gln Ile Glu Gln Val Ile Leu Val Gly
370                 375                 380

Gly Pro Thr Arg Val Pro Lys Val Gln Glu Val Leu Leu Lys Pro Val
385                 390                 395                 400

Gly Lys Glu Glu Leu Gly Lys Asn Ile Asn Ala Asp Glu Ala Ala Ala
                405                 410                 415

Met Gly Ala Val Tyr Gln Ala Ala Leu Ser Lys Ala Phe Lys Val
                420                 425                 430

Lys Pro Phe Val Val Arg Asp Ala Val Ile Tyr Pro Ile Leu Val Glu
            435                 440                 445

Phe Thr Arg Glu Val Glu Glu Pro Gly Leu Arg Ser Leu Lys His
            450                 455                 460

Asn Lys Arg Val Leu Phe Ser Arg Met Gly Pro Tyr Pro Gln Arg Lys
465                 470                 475                 480

Val Ile Thr Phe Asn Arg Tyr Ser His Asp Phe Asn Phe His Ile Asn
```

-continued

```
                485                 490                 495
Tyr Gly Asp Leu Gly Phe Leu Gly Pro Glu Asp Leu Arg Val Phe Gly
                500                 505                 510

Ser Gln Asn Leu Thr Thr Val Lys Leu Lys Gly Val Gly Glu Ser Phe
                515                 520                 525

Lys Lys Tyr Pro Asp Tyr Glu Ser Lys Gly Ile Lys Ala His Phe Asn
                530                 535                 540

Leu Asp Glu Ser Gly Val Leu Ser Leu Asp Arg Val Glu Ser Val Phe
545                 550                 555                 560

Glu Thr Leu Val Glu Asp Ser Pro Glu Glu Ser Thr Leu Thr Lys
                    565                 570                 575

Leu Gly Asn Thr Ile Ser Ser Leu Phe Gly Gly Thr Ser Ser Asp
                580                 585                 590

Ala Lys Glu Asn Gly Thr Asp Ala Val Gln Glu Glu Glu Ser Pro
                595                 600                 605

Ala Glu Gly Ser Lys Asp Glu Pro Ala Glu Gln Gly Glu Leu Lys Glu
                610                 615                 620

Glu Ala Glu Ala Pro Met Glu Asp Thr Ser Gln Pro Pro Ser Glu
625                 630                 635                 640

Pro Lys Gly Asp Ala Ala Arg Glu Gly Glu Thr Pro Asp Glu Lys Glu
                    645                 650                 655

Ser Gly Asp Lys Ser Glu Ala Gln Lys Pro Asn Glu Lys Gly Gln Ala
                660                 665                 670

Gly Pro Glu Gly Val Pro Pro Ala Pro Glu Glu Lys Gln Lys
                675                 680                 685

Pro Ala Arg Lys Gln Lys Met Val Glu Glu Ile Gly Val Glu Leu Ala
                690                 695                 700

Val Leu Asp Leu Pro Asp Leu Pro Glu Asp Glu Leu Ala His Ser Val
705                 710                 715                 720

Gln Lys Leu Glu Asp Leu Thr Leu Arg Asp Leu Glu Lys Gln Glu Arg
                    725                 730                 735

Glu Lys Ala Ala Asn Ser Leu Glu Ala Phe Ile Phe Glu Thr Gln Asp
                740                 745                 750

Lys Leu Tyr Gln Pro Glu Tyr Gln Glu Val Ser Thr Glu Glu Gln Arg
                755                 760                 765

Glu Glu Ile Ser Gly Lys Leu Ser Ala Thr Ser Thr Trp Leu Glu Asp
770                 775                 780

Glu Gly Phe Gly Ala Thr Thr Val Met Leu Lys Asp Lys Leu Ala Glu
785                 790                 795                 800

Leu Arg Lys Leu Cys Gln Gly Leu Phe Phe Arg Val Glu Glu Arg Arg
                    805                 810                 815

Lys Trp Pro Glu Arg Leu Ser Ala Leu Asp Asn Leu Leu Asn His Ser
                820                 825                 830

Ser Ile Phe Leu Lys Gly Ala Arg Leu Ile Pro Glu Met Asp Gln Ile
                835                 840                 845

Phe Thr Asp Val Glu Met Thr Thr Leu Glu Lys Val Ile Asn Asp Thr
                850                 855                 860

Trp Thr Trp Lys Asn Ala Thr Leu Ala Glu Gln Ala Lys Leu Pro Ala
865                 870                 875                 880

Thr Glu Lys Pro Val Leu Leu Ser Lys Asp Ile Glu Ala Lys Met Met
                    885                 890                 895

Ala Leu Asp Arg Glu Val Gln Tyr Leu Leu Asn Lys Ala Lys Phe Thr
                900                 905                 910
```

```
Lys Pro Arg Pro Arg Pro Lys Asp Lys Asn Gly Thr Arg Thr Glu Pro
        915                 920                 925

Pro Leu Asn Ala Ser Ala Gly Asp Gln Glu Glu Lys Val Ile Pro Pro
        930                 935                 940

Thr Gly Gln Thr Glu Glu Ala Lys Ala Ile Leu Glu Pro Asp Lys Glu
945                 950                 955                 960

Gly Leu Gly Thr Glu Ala Ala Asp Ser Glu Pro Leu Glu Leu Gly Gly
                    965                 970                 975

Pro Gly Ala Glu Ser Glu Gln Ala Glu Gln Thr Ala Gly Gln Lys Arg
                980                 985                 990

Pro Leu Lys Asn Asp Glu Leu
        995
```

(2) INFORMATION FOR SEQ ID NO:4:

(i) SEQUENCE CHARACTERISTICS:
        (A) LENGTH: 3252 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) IDENTIFICATION METHOD: E (xi) SEQUENCE DESCRIPTION: SEQ ID NO:4:

```
TGAGGATGGA GCAGCGGTCG GGCCGCGGCT CCTAGGGGAG GCAGCGTGCT AGCTTCGGGG      60

GCGGGCCAGT AGCGGGAGCG AGGGCCGTAC GGACACCGGT CCCTTCGGCC TTGAAGTTCA     120

GGCGCTGAGC TGCCCCCTCG CGCTCGGGGT GGGCCGGAAT CCATTTCTGG GAGTGGGATC     180

TTCCACCTTC ATCAGGGTCA CAATGGCAGC TACAGTAAGG AGGCAGAGGC CAAGGAGGCT     240

ACTCTGTTGG GCCTTGGTGG CTGTCCTCTT GGCAGACCTG TTGGCACTGA GTGACACACT     300

GGCTGTGATG TCTGTGGACC TGGGCAGTGA ATCCATGAAG GTGGCCATTG TCAAGCCTGG     360

AGTGCCCATG GAGATTGTAT TGAACAAGGA ATCTCGGAGG AAAACTCCGG TGACTGTGAC     420

CTTGAAGGAA AACGAAAGGT TTCTAGGTGA CAGTGCAGCT GGCATGGCCA TCAAGAACCC     480

AAAGGCTACG CTCCGTTATT TCCAGCACCT CCTTGGAAAG CAGGCAGATA ACCCTCATGT     540

GGCTCTTTAC CGGTCCCGTT TCCCAGAACA TGAGCTCAAT GTTGACCCAC AGAGGCAGAC     600

TGTGCGCTTC CAGATCAGTC CGCAGCTGCA GTTCTCTCCC GAGGAGGTGC TGGGCATGGT     660

TCTCAACTAC TCCCGTTCCC TGGCTGAAGA TTTTGCAGAA CAACCTATTA GGATGCAGT     720

GATCACCGTG CCAGCCTTTT TCAACCAGGC CGAGCGCCGA GCTGTGCTGC AGGCTGCTCG     780

TATGGCTGGC CTCAAGGTGC TGCAGCTCAT CAATGACAAC ACTGCCACAG CCCTCAGCTA     840

TGGTGTCTTC CGCCGGAAAG ATATCAATTC CACTGCACAG AATATCATGT CTATGACAT      900

GGGCTCGGGC AGCACTGTGT GTACCATCGT GACCTACCAA ACGGTGAAGA CTAAGGAGGC     960

TGGGACGCAG CCACAGCTAC AGATCCGGGG CGTGGGATTT GACCGCACCC TGGGTGGCCT    1020

GGAGATGGAG CTTCGGCTGC GAGAGCACCT GGCTAAGCTC TTCAATGAGC AGCGCAAGGG    1080

CCAGAAAGCC AAGGATGTTC GGGAAAACCC CCGAGCCATG GCCAAACTGC TTCGGGAAGC    1140

CAATCGGCTT AAAACCGTCC TGAGTGCCAA TGCTGATCAC ATGGCACAGA TTGAAGGCTT    1200

GATGGACGAT GTGGACTTCA AGGCAAAAGT AACTCGAGTG GAGTTTGAGG AGCTGTGTGC    1260

AGATTTGTTT GATCGAGTGC CTGGGCCTGT ACAGCAGGCC CTGCAGAGTG CTGAGATGAG    1320
```

```
CCTGGATCAA ATTGAGCAGG TGATCCTGGT GGGTGGGCCC ACTCGTGTTC CCAAAGTTCA    1380

AGAGGTGCTG CTGAAGCCTG TGGGCAAGGA GGAACTAGGA AAGAACATCA ATGCCGATGA    1440

AGCAGCTGCC ATGGGGGCCG TGTACCAGGC AGCGGCACTG AGCAAAGCCT TCAAAGTGAA    1500

GCCATTTGTT GTGCGTGATG CTGTTATTTA CCCCATCCTG GTGGAGTTCA CAAGGGAGGT    1560

GGAGGAGGAG CCTGGGCTTC GAAGCCTGAA GCACAATAAA CGTGTGCTCT TCTCCCGAAT    1620

GGGGCCCTAC CCTCAGCGCA AAGTCATCAC CTTTAACCGA TACAGCCATG ATTTCAACTT    1680

TCACATCAAC TACGGTGACC TGGGCTTCCT GGGGCCTGAG GATCTTCGGG TATTTGGCTC    1740

CCAGAATCTG ACCACAGTGA AACTAAAAGG TGTGGGAGAG AGCTTCAAGA AATATCCTGA    1800

CTATGAGTCC AAAGGCATCA AGGCCCACTT TAACCTAGAC GAGAGTGGAG TGCTCAGTTT    1860

AGACAGGGTG GAGTCCGTAT TCGAGACCCT GGTGGAGGAC AGCCCAGAGG AAGAGTCTAC    1920

TCTTACCAAA CTTGGCAACA CCATTTCCAG CCTGTTTGGC GGTGGTACCT CATCAGATGC    1980

CAAAGAGAAT GGTACTGATG CTGTACAGGA GGAGGAGGAG AGCCCTGCTG AGGGGAGCAA    2040

GGATGAGCCT GCAGAACAGG GGGAACTCAA GGAGGAAGCT GAAGCCCCAA TGGAGGATAC    2100

CTCCCAGCCT CCACCCTCTG AGCCTAAGGG GGATGCAGCC CGTGAGGGAG AAACACCTGA    2160

TGAAAAAGAA AGTGGGGACA AGTCTGAGGC CCAGAAGCCC AATGAGAAGG GGCAGGCAGG    2220

GCCTGAGGGT GTCCCTCCAG CTCCCGAGGA AGAAAAAAAG CAGAAACCTG CCCGGAAGCA    2280

GAAAATGGTG GAGGAGATAG GTGTGGAACT GGCTGTCTTG GACCTGCCAG ACTTGCCAGA    2340

GGATGAGCTG GCCCATTCCG TGCAGAAACT TGAGGACTTG ACCCTGCGAG ACCTTGAAAA    2400

GCAGGAGAGG GAGAAAGCTG CCAACAGCTT AGAAGCTTTT ATCTTTGAGA CCCAGGACAA    2460

ACTGTACCAA CCTGAGTACC AGGAAGTGTC CACTGAGGAA CAACGGGAGG AGATCTCTGG    2520

AAAACTCAGT GCCACTTCTA CCTGGCTGGA GGATGAGGGA TTTGGAGCCA CCACTGTGAT    2580

GTTGAAGGAC AAGCTGGCTG AGCTGAGAAA GCTGTGCCAA GGGCTGTTTT TTCGGGTGGA    2640

AGAGCGCAGG AAAATGGCCAG AGCGGCTTTC AGCTCTGGAT AATCTCCTCA ATCACTCCAG    2700

CATTTTCCTC AAGGGTGCCC GACTCATCCC AGAGATGGAC CAGATCTTCA CTGACGTGGA    2760

GATGACAACG TTGGAGAAAG TCATCAATGA CACCTGGACC TGGAAGAATG CAACCCTGGC    2820

CGAGCAGGCC AAGCTTCCTG CCACAGAGAA ACCCGTGCTG CTTTCAAAAG ACATCGAGGC    2880

CAAAATGATG GCCCTGGACC GGGAGGTGCA GTATCTACTC AATAAGGCCA AGTTTACTAA    2940

ACCCCGGCCA CGGCCCAAGG ACAAGAATGG CACCCGGACA GAGCCTCCCC TCAATGCCAG    3000

TGCTGGTGAC CAAGAGGAAA AGGTCATTCC ACCTACAGGC CAGACTGAAG AGGCGAAGGC    3060

CATCTTAGAA CCTGACAAAG AAGGGCTTGG TACAGAGGCA GCAGACTCTG AGCCTCTGGA    3120

ATTAGGAGGT CCTGGTGCAG AATCTGAACA GGCAGAGCAG ACAGCAGGGC AGAAGCGGCC    3180

TTTGAAGAAT GATGAGCTGT GACCCCGCGC CTCCGCTCCA CTTGCCTCCA GCCCCTTCTC    3240

CTACCACCTC TA                                                      3252
```

(2) INFORMATION FOR SEQ ID NO:5:

(i) SEQUENCE CHARACTERISTICS:
            (A) LENGTH: 31 amino acids
            (B) TYPE: amino acid
            (D) TOPOLOGY: linear (ii) MOLECULE TYPE: peptide (xi) SEQUENCE DESCRIPTION: SEQ ID NO:5:

```
Leu Ala Val Met Ser Val Asp Leu Gly Ser Glu Ser Met Lys Val Ala
             5                  10                  15
Ile Val Lys Pro Gly Val Pro Met Glu Ile Val Leu Asn Lys Glu
             20                  25                  30
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid, synthetic
        nucleic acid (xi) SEQUENCE DESCRIPTION: SEQ ID NO:6:

```
AATACGACTC ACTATAGGGA                                              20
```

(2) INFORMATION FOR SEQ ID NO:7:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:7:

```
Lys Pro Gly Val Pro Met Glu
             5
```

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid, synthetic
        nucleic acid (ix) FEATURE:
        (A) NAME/KEY: misc_feature
        (B) LOCATION: 1..20
        (D) OTHER INFORMATION: /note= "residues 6 and 9 are
            inosine"

(xi) SEQUENCE DESCRIPTION: SEQ ID NO:8:

```
AARCCNGGNG TNCCNATGGA                                              20
```

(2) INFORMATION FOR SEQ ID NO:9:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:9:

```
Lys Pro Gly Val Pro Met Glu Ile Val Leu Asn Lys Glu
             5                  10
```

(2) INFORMATION FOR SEQ ID NO:10:

(i) SEQUENCE CHARACTERISTICS:
        (A) LENGTH: 20 base pairs

-continued

```
        (B) TYPE: nucleic acid
        (C) STRANDEDNESS: single
        (D) TOPOLOGY: linear (ii) MOLECULE TYPE: other nucleic acid, synthetic
            nucleic acid (xi) SEQUENCE DESCRIPTION: SEQ ID NO:10:

GCACCCTTGA GGAAAATGCT                                               20

(2) INFORMATION FOR SEQ ID NO:11:

(i) SEQUENCE CHARACTERISTICS:
        (A) LENGTH:   20 base pairs
        (B) TYPE: nucleic acid
        (C) STRANDEDNESS: single
        (D) TOPOLOGY: linear (ii) MOLECULE TYPE: other nucleic acid, synthetic
            nucleic acid (xi) SEQUENCE DESCRIPTION: SEQ ID NO:11:

CCCAGAAGCC CAATGAGAAG                                               20

(2) INFORMATION FOR SEQ ID NO:12:

(i) SEQUENCE CHARACTERISTICS:
        (A) LENGTH:   2861 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:12:

GAAAGAAGTA GACATGGGAG ACTTCATTTT GTTCTGTACT AAGAAAAATT CTTCTGCCTT    60

GGGATGCTGT TGATCTATGA CCTTACCCCC AACCCTGTGC TCTCTGAAAC ATGTGCTGTG   120

TCCACTCAGG GTTAAATGGA TTAAGGGCGG TGCAAGATGT GCTTTGTTAA ACAGATGCTT   180

GAAGGCAGCA TGCTCGTTAG GAGTCATCAC CACTCCCTAA TCTCAAGTAC CCAGGGACAC   240

AAACACTGCG GAAGGCCACA GGGTCCTCTG CCTAGGAAAG CCAGAGACCT TGTTCACTT    300

GTTTATCTGC TGACCTTCCC TCCACTATTG TCCTATGACC CTGCCAAATC CCCCTCTGCC   360

AGAAACACCC AAGAATGATC AATAAAAAAA AAAAAAAAA AAAAAGGAAG AATAGACTCT    420

CTCTGGGACT GCCAATAATT TTTCCTTCTA AGCATAGACA CCGGACCACT CTCCACCTAA   480

GCATCACGAA AAATGTAGAG AAAGGAAGAG CTAAGAGCTC CTTAAACAAG TTCAGGCTTG   540

ACACAACCCT GGCCCTGACA GCCAGGGTCT TCAAGCGGGC CTTTCTGTGA AGGGTGGCCA   600

GGCATCAACT TAGTAGGAGA GAAAACAGAT GACTTATTTC CATCCACACT TAAGGAAAAT   660

GCAGTCTCCA AGGACTGCGT ACATTTCTTT TTCGAGAAGG AGTCTCGCTG TTGTCGCCCA   720

GGCTGGAGTG CAGTGGCGCA GTCTGGGCTC ACAGCAACCT CTGCCTCCCG GATTCAAGCA   780

ATTCTCCTGC CTCAGCCTCG TGAGTAGCTG GGATTACAGG CACCCGCCAC CACGCCTGGC   840

TAATTTTTGT AGTTTTGGTA GAGACGGGGT TTCACCATGT TGGCCAGGCT GGTCTCGAAC   900

TCCTGACCTC CAGTGATTCG CCCGCCTTGG CCTCCCAAAA TGCTGGGATT ACAGGCGTGA   960

GCCACCGCGC CCGGGCGACT GCGCACATTT CTATGGAGCT GTAAGTTAAA AGAGAAGGCA  1020

GTGAGGTGCT TCTGTCATTC TATGACAGAA ACAGCTAAAG AGTAGAGAAA TGTTCACAAG  1080

ATTTAATAGA ACAGAAATAG GAGAAGGTGC ACACAAGCTC AACCAACTAT AGCCTCACAA  1140

ATAAAGTGT CTTTTGTGTG TAGTACTTAA GTTTGGAATA TTCTTTCTTA TACAAATGAG    1200
```

-continued

```
TGGGGCTTAA CCTAAGAAAT CCTGGCCAGA TTCTGCGACG AATGCATCGG TTATCTCTGA    1260

CCCATCAGCA AACATCTTTT TCTGTGGCTT CAGTTTCCTC AGTAAAACAG AGGGGGTTGC    1320

GACGGACTCA GTCCGAGGCA CAGCCATTCT CCAACGTCTA TCCAAAGCCT AGGGCACCTC    1380

AATACTAACC GGCAGGCCAG CGCCCCCTCC GCGGGGCTGC GGACAGGACG CCTGTTATTC    1440

CATTCCTCGG CCGGGCTCTA CAGGTGACCG GAAGAAGAGC CCCGAGTGCG GGACTGCAGT    1500

GCGCCCGACC TGCTCTAGGC GCAGGTCACT CCCGAACCCC GGCAGCAAAG CATCCAGCGC    1560

CGGAAAAGGT CCCGCGGTCG CCCCGGGGCC GGCGCTGGGG AGGAAGGAGT GGAGCGCGCT    1620

GGCCCCGTGA CGTGGTCCAA TCCCAGGCCG ACGCCGGCTG CTTCTGCCCA ACCGGTGGCT    1680

GGTCCCCTCC GCCGCCCCCA TTACAAGGCT GGCAAAGGGA GGGGGCGGGG CCTGGGACGT    1740

GGTCCAATGA GTACGCGCGC CGGGGCGGCG GGGGCGGGGC CGGGCGCGCA GCGCAGGGCC    1800

GGGCGGCCGA GGCTCCAATG AGCGCCCGCC GCGTCCGGGG CCGGCTGGTG CGCGAGACGC    1860

CGCCGAGAGG TTGGTGGCTA ATGTAACAGT TTGCAAACCG AGAGGAGTTG TGAAGGGCGC    1920

GGGTGGGGGG CGCTGCCGGC CTCGTGGGTA CGTTCGTGCC GCGTCTGTCC CAGAGCTGGG    1980

GCCGCAGGAG CGGAGGCAAG AGGTAGCGGG GGTGGATGGA GGTGCGGGCC GGCCACCCCT    2040

CCTAGGGGAG ACAGCGTGCG AGCTCCGGGG GCGGGTCGGG AGCGCAAGGG AGGGCCGCGC    2100

GGACGCCGGG CGCTCGGCCT CGCACCGGGG GGCACGCAGC TCGGCCCCCG GTCTGTCCCC    2160

ACTTGCTGGG GCGGGCCGGG ATCCGTTTCC GGGAGTGGGA GCCGCCGCCT TCGTCAGGTG    2220

GGGTTTAGGT GAACACCGGG TAACGGCTAC CCGCCGGGCG GGGAACCTTA CCGCCCCTGG    2280

CACTGCGTCT GTGGGCACAG CGGGGCCGGG GAGTGAGCTG GGAAAGGGGA GGGGGCGGGA    2340

CAACCCGCAG GGATGCCGAG GAGGAGATAG GCCTTTCCTT CATCCTAGCT ACCCCCAACG    2400

TCATTACCTT TCTCTTCCCG TCCAGGCCCA GCTGGCTTTC CCCGTCAGCG GGGGAGCTCC    2460

AGGTGTGGGG AGGTGGTTGA GCCCTGGGCG GGGATCCCTG GCCGCACCCC AGGTGTCTGA    2520

CAACAGGCAC AGTGCTGCGG TGCGCCACTC ACTGCCTGTG TGGTGGACAA AAGGCTCGGG    2580

TCTCCTTTCT CTTGTCCTGT TAGCTTCTCT GTTTAGGGAT GTGGCAAAGC CGAGGACCCA    2640

TGCTCTTTCA CTTGGGCCTT TGTGTGGGCG CTGCTGGGAT GATTAGAGAA TGGTTTGTAC    2700

CCATCAGGAG GGAGAAGGGG AGAAGTAGGC TGATCTGCCC TGGGTAAGAA TGAAGTAGAT    2760

ATGAATCTTA CAGCCTCTCC GTTCTGGGAT GTGATTCTGT CTCCTTCACT CCGGGTATCC    2820

AGTTTTAAGT GTTTTCTTTC TTCGCCTCCC CCAGGGGCAC T                       2861
```